US012575719B2

(12) United States Patent
Suzuki

(10) Patent No.: US 12,575,719 B2
(45) Date of Patent: Mar. 17, 2026

(54) STERILE MEDICAL DEVICE PACKAGE, MEDICAL DEVICE SYSTEM, STERILIZATION METHOD FOR MEDICAL DEVICE, AND OPENING METHOD FOR STERILE MEDICAL DEVICE PACKAGE

(71) Applicant: OLYMPUS MEDICAL SYSTEMS CORP., Tokyo (JP)

(72) Inventor: Takeo Suzuki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 419 days.

(21) Appl. No.: 18/106,562

(22) Filed: Feb. 7, 2023

(65) Prior Publication Data

US 2023/0255451 A1     Aug. 17, 2023

Related U.S. Application Data

(60) Provisional application No. 63/309,068, filed on Feb. 11, 2022.

(51) Int. Cl.
*A61B 1/00*          (2006.01)

(52) U.S. Cl.
CPC ...... *A61B 1/00144* (2013.01); *A61B 1/00103* (2013.01)

(58) Field of Classification Search
CPC . A61B 1/00103; A61B 1/00144; A61B 50/30; A61B 2050/3004; A61B 2050/3005; A61B 2050/3008; A61M 25/002; A61L 2202/18; B65D 17/00; B65D 31/12; B65D 33/00; B65D 33/008

USPC ...................................... 383/38, 40; 206/222
See application file for complete search history.

(56) References Cited

U.S. PATENT DOCUMENTS

| | | | | |
|---|---|---|---|---|
| 2,157,169 A | * | 5/1939 | Foster | A47J 36/30 206/222 |
| 4,256,256 A | * | 3/1981 | Meyers | B65D 31/12 53/550 |
| 6,594,971 B1 | | 7/2003 | Addy et al. | |
| 8,986,265 B2 | | 3/2015 | Nestenborg et al. | |
| 2007/0095679 A1 | * | 5/2007 | Nakamura | A61B 50/30 206/210 |
| 2011/0233079 A1 | * | 9/2011 | Macinnes | A61M 5/002 283/106 |

(Continued)

FOREIGN PATENT DOCUMENTS

| | | |
|---|---|---|
| JP | H04-250172 A | 9/1992 |
| JP | H04-279141 A | 10/1992 |

(Continued)

*Primary Examiner* — Aaron B Fairchild
(74) *Attorney, Agent, or Firm* — Morgan, Lewis & Bockius LLP

(57)          ABSTRACT

A sterile medical device package includes a packaging member having an interior space, and a disinfectant solution package located in a first section of the interior space. A second section of the interior space is configured to contain a sterile medical device. The disinfectant solution package is configured to contain a disinfectant solution. The packaging member is configured to form a first opening and the disinfectant solution package is configured to form a second opening. A part of the disinfectant solution package is fixed to the packaging member such that the second opening is formed in conjunction with forming the first opening.

18 Claims, 7 Drawing Sheets

(56)          References Cited

U.S. PATENT DOCUMENTS

2013/0236128 A1 *   9/2013   Bray ...................... B65D 31/02
                                                                  383/69
2015/0257632 A1 *   9/2015   Ramsey ............. A61B 1/00144
                                                                  206/204

FOREIGN PATENT DOCUMENTS

| JP | 2002-533191 | A | 10/2002 |
| JP | 2005-523779 | A | 8/2005 |
| JP | 2009-118882 | A | 6/2009 |
| JP | 2009-118883 | A | 6/2009 |
| JP | 2009-136612 | A | 6/2009 |
| JP | 2009-136613 | A | 6/2009 |
| JP | 2009-136614 | A | 6/2009 |
| JP | 2011-177457 | A | 9/2011 |

* cited by examiner

STERILE MEDICAL DEVICE PACKAGE, MEDICAL DEVICE SYSTEM, STERILIZATION METHOD FOR MEDICAL DEVICE, AND OPENING METHOD FOR STERILE MEDICAL DEVICE PACKAGE

RELATED APPLICATION DATA

This application is based on and claims priority under 35 U.S.C. § 119 to U.S. Provisional Application No. 63/309, 068 filed on Feb. 11, 2022, the entire contents of which are incorporated herein by reference.

FIELD OF DISCLOSURE

The present disclosure relates to a sterile medical device package inside which a medical device is placed to be kept sterile, a medical device system for placing the medical device inside the sterile medical device package, a sterilization method for the medical device, and an opening method for the sterile medical device package.

BACKGROUND

Generally, endoscopes include reusable endoscopes that are used several times by being subjected to reprocessing, and single-use endoscopes that are used just once.

A medical device such as the single-use endoscope is sterilized while contained in a sterile package, and is shipped in a sterile state. The single-use endoscope is disposed of after being used once.

For example, Japanese Patent Application Laid-Open Publication No. 2002-533191 describes a configuration according to which an endoscope is contained inside a sterile package that passes a sterilizing gas but is impervious to microorganisms.

SUMMARY OF THE DISCLOSURE

A sterile medical device package according to the present disclosure includes a packaging member having an interior space, and a disinfectant solution package located in a first section of the interior space. A second section of the interior space is configured to contain a sterile medical device. The disinfectant solution package is configured to contain a disinfectant solution. The packaging member is configured to form a first opening and the disinfectant solution package is configured to form a second opening. A part of the disinfectant solution package is fixed to the packaging member such that the second opening is formed in conjunction with forming the first opening.

A packaging method according to the present disclosure includes placing a sterile medical device inside a package, placing a disinfectant solution inside a disinfectant solution package placed in the package, sealing the package and the disinfectant solution containing package with a common seal, forming a preferential opening portion on the package and disinfectant solution package. The preferential opening portion opens the common seal to simultaneously open the package and the disinfectant solution package.

A method of opening a sterile medical device according to the present disclosure includes holding the sterile medical device package, and opening the sterile medical device package by an opening operation. The sterile medical device package includes a packaging member, a sterile medical device, and a disinfectant solution package containing a disinfectant solution. A portion of the disinfectant solution package is fixed to the packaging member such that the opening operation opens both the packaging member and the disinfectant solution package.

DETAILED DESCRIPTION

Figure 1:
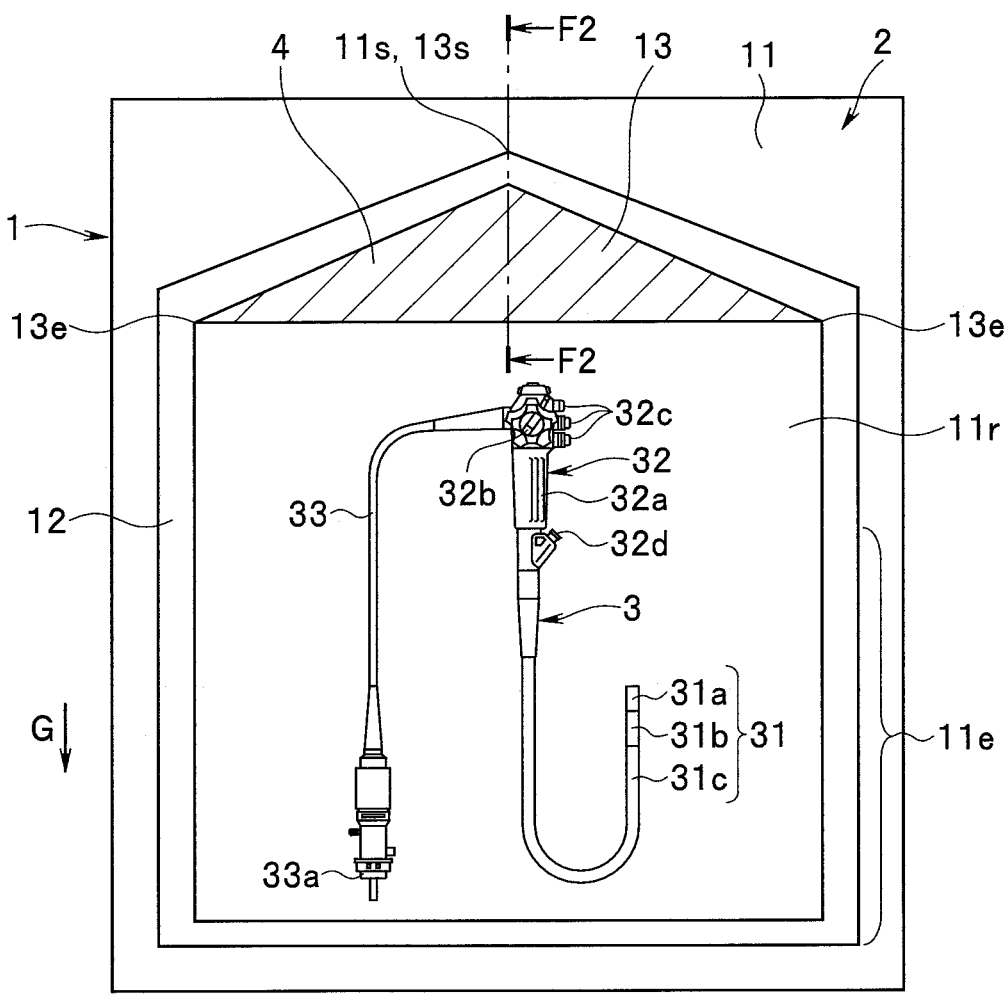
FIG. 1 is a diagram showing a medical device system according to a first embodiment of the present disclosure.

Generally, even a single-use endoscope comes into contact with air in an endoscopic examination room when a sterile package is opened before insertion into a subject. Accordingly, there is a possibility of environmental bacteria such as floating bacteria in the air, falling bacteria and the like getting attached to a surface of a medical device.

According to embodiments described below, there may be provided a sterile medical device package that is capable of reducing the possibility of environmental bacteria getting attached to a medical device even when the sterile medical device package is opened, a medical device system, a sterilization method for the medical device, and an opening method for the sterile medical device package.

In the following, embodiments of the present disclosure will be described with reference to the drawings. However, the present disclosure is not limited to the embodiments described below.

Note that, in the drawings, same or corresponding components are denoted by same reference signs as appropriate. Furthermore, the drawings are schematic, and it should be noted that relationships between lengths of components, ratios of lengths of components, the numbers of components and the like in one drawing may be different from reality for the sake of simplicity of description. Moreover, relationships or ratios of lengths may be different between a plurality of drawings.

First Embodiment

Figure 2:
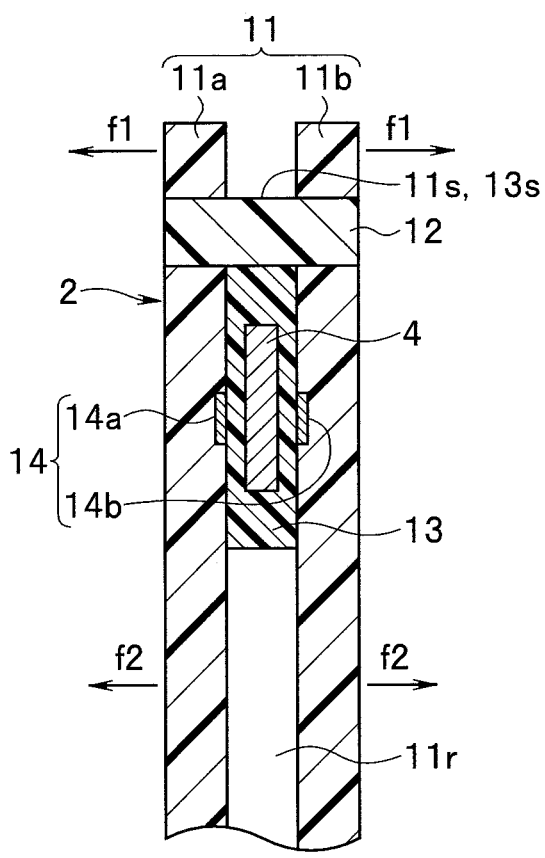
FIG. 2 is a cross-sectional view according to the first embodiment, taken along F2-F2 in FIG. 1.

FIGS. 1 and 2 show a first embodiment of the present disclosure, and FIG. 1 is a diagram showing a medical device system 1 of the first embodiment.

The medical device system 1 includes a sterile medical device package 2, and a medical device.

FIG. 1 shows an example where the medical device that is placed inside the sterile medical device package 2 is an endoscope 3.

The endoscope 3 is a device used to observe and treat a subject. The endoscope 3 includes a thin, elongated insertion section 31 that is to be inserted inside a subject, an operation section 32 that is provided continuously to a proximal end side of the insertion section 31, and a universal cable 33 that extends from the operation section 32. Note that the subject into which the insertion section 31 is inserted is assumed to be, but not limited to, a living thing such as a human being or an animal, and may alternatively be a non-living thing such as a machine or a building.

The insertion section 31 includes, in order from a distal end to a proximal end, a distal end portion 31a, a bending portion 31b, and a tubular portion 31c.

The distal end portion 31a includes an observation system and an illumination system, and the illumination system radiates illumination light on a subject, and the observation system picks up return light from the subject.

The bending portion 31b is provided continuously to a proximal end side of the distal end portion 31a, and is capable of bending in two directions, or in four directions of up, down, left and right. When the bending portion 31b is bent, a direction of the distal end portion 31a is changed, and a direction of observation by the observation system and a radiation direction of illumination light by the illumination system are changed. Moreover, the bending portion 31b is also bent to increase insertability of the insertion section 31 inside the subject.

The tubular portion 31c is a tubular part that connects a proximal end of the bending portion 31b and a distal end of the operation section 32. The tubular portion 31c may be rigid such that the insertion section 31 does not flex, or may be flexible such that the insertion section 31 flexes according to a shape of the subject into which insertion is performed. An endoscope with a rigid insertion section is generally referred to as a rigid endoscope, and an endoscope with a flexible insertion section is generally referred to as a flexible endoscope. For example, the rigid endoscope and the flexible endoscope in a medical field are defined in ISO8600-1:2015.

The operation section 32 is a part that is provided continuously to the proximal end side of the insertion section 31, and that is held with a hand to perform various operations related to the endoscope 3. For example, the operation section 32 includes a grasping portion 32a, a bending operation lever 32b, a plurality of operation buttons 32c, and a treatment instrument insertion opening 32d.

The grasping portion 32a is a part that is used by an operator to hold the endoscope 3 in a palm.

The bending operation lever 32b is an operation device for performing an operation of bending the bending portion 31b, and is operated by, for example, a thumb or the like of a hand holding the grasping portion 32a.

The plurality of operation buttons 32c include a gas-feeding/liquid-feeding button, a suction button, and a button related to image pickup, for example. The gas-feeding/liquid-feeding button is a button for performing an operation of cleaning an observation window of the distal end portion 31a by feeding gas and liquid to the observation window via a gas-feeding/liquid-feeding channel, not shown. The suction button is a button for performing an operation of sucking fluid, mucous membrane and the like from inside the subject via, for example, a treatment instrument channel that serves also as a suction channel. The button related to image pickup is a button switch for performing a release operation, for example.

The treatment instrument insertion opening 32d is an opening on a proximal end side of the treatment instrument channel, and is provided in a side surface on a distal end side of the grasping portion 32a, for example. Various treatment instruments such as forceps are inserted into the treatment instrument channel via the treatment instrument insertion opening 32d. An opening on a distal end side of the treatment instrument channel is provided in the distal end portion 31a to allow a distal end of a treatment instrument to protrude to apply various treatments.

The universal cable 33 extends from a side surface on a proximal end side of the operation section 32, and is connected to an endoscope processor and a light source device, not shown, via a connector 33a.

The present embodiment and other embodiments described below describe, as examples, cases where the medical device to be contained inside the sterile medical device package 2 is the endoscope 3, but such cases are not restrictive. Here, a single-use endoscope that is disposed of after being used just once is cited as an example of the endoscope 3.

For example, the medical device may be a treatment instrument for endoscope, a treatment instrument for laparoscope such as scissors or grasping forceps, an energy treatment instrument such as an electric knife or an ultrasound coagulation cutting device, an ultrasound probe, a catheter such as a urinary catheter, a trocar, a mouthpiece, a sliding tube, a sheath, or an implantable device (such as a pacemaker). Moreover, the endoscope 3 as the medical device may be a regular endoscope or may be an ultrasound endoscope.

The sterile medical device package 2 includes a packaging member 11, a seal 12, a disinfectant solution containing member 13 (disinfectant solution package), and a pull portion 14. The packaging member 11 has an interior space. A disinfectant solution package 13 is located in a first section of the interior space. A second section of the interior space is configured to contain a sterile medical device. The disinfectant solution package 13 is configured to contain a disinfectant solution. The packaging member 11 is configured to form a first opening and the disinfectant solution package 13 is configured to form a second opening. A part of the disinfectant solution package 13 is fixed to the packaging member 11 such that the second opening is formed in conjunction with forming the first opening.

FIG. 2 is a cross-sectional view according to the first embodiment, taken along F2-F2 in FIG. 1.

The packaging member 11 is a bag-shaped member inside which the endoscope 3 that is sterilized is placed. The packaging member 11 of the present embodiment is formed into a bag shape by sticking a first sheet 11a and a second sheet 11b together by the seal 12. The first sheet 11a and the second sheet 11b are connected to form a bag shape, and the first opening is formed by separating the first sheet 11a and the second sheet 11b.

At least one of the first sheet 11a or the second sheet 11b includes a part that is transparent or semi-transparent and that allows a medical device that is contained inside to be viewed. Moreover, at least one of the first sheet 11a or the second sheet 11b is formed to pass a sterilizing gas such that the medical device that is contained inside can be sterilized, while being impervious to bacteria. The medical device such as the endoscope 3 is thus sterilized while contained in the sterile medical device package 2.

The seal 12 seals the packaging member 11, and keeps the endoscope 3 contained inside the packaging member 11 sterile. For example, the seal 12 is formed as a heat seal that is obtained by melt-bonding the first sheet 11a and the second sheet 11b by heating and pressurization. For example, the seal 12 is formed as a pentagonal closed curve that has a shape where a triangle is joined to one side of a rectangle.

For example, an apex of a triangular part of the pentagonal seal 12 is an opening action start point 11s (first end) where an action of opening the packaging member 11 is started. Furthermore, the action of opening the packaging member 11 is ended when a state where the endoscope 3 may be taken out is reached. Accordingly, an opening action end point 11e (second end) where the action of opening is ended does not have to be limited to one point, but may be any point within a range shown in FIG. 1, for example. The packaging member 11 is configured to form the first opening by including a first portion that opens upon an application of an external force. The disinfectant solution package 13 is configured to form the second opening by including a second portion that opens upon the application of the external force. The first portion includes at least a portion of the second portion. The disinfectant solution package 13 includes the first end 13s and the second end 13e. The first end 13s is a starting point for forming the second opening and the second end 13e is an ending point for forming the second opening. The first end 13s and the second end 13e are located on a part of the packaging member 11. The disinfectant solution package 13 is configured to form the second opening in a first area. The first area includes a first area section and a second area section. The first area section has a first mechanical strength and includes one of the first end 13s and the second end 13e. The second area section has a second mechanical strength that is lower than the first mechanical strength. The disinfectant solution package 13 includes a third sheet and a fourth sheet. A first part of the third sheet is fixed to the first sheet 11a, and a first part of the fourth sheet is fixed to the second sheet 11b, and a second part of the third sheet is fixed to a second part of the fourth sheet. The second opening is formed by separating one of (i) a portion of the first part of the third sheet from the first sheet 11a, (ii) a portion of the first part of the fourth sheet from the second sheet 11b in conjunction with separating the first sheet 11a and the second sheet 11b, and (iii) a portion of the second part of the third sheet from a portion of the second part of the fourth sheet.

The disinfectant solution containing member 13 is formed into a bag shape, and is provided in a space 11r inside the packaging member 11 that is sealed by the seal 12. A volatile disinfectant solution 4 is contained inside the bag shape of the disinfectant solution containing member 13. Examples of the disinfectant solution 4 include, but are not limited to, ethanol, isopropanol, oxydol (hydrogen peroxide), hypochlorous acid, or a solution obtained by diluting any of those listed with distilled water. The disinfectant solution package 13 includes a first area and a second area. The first area has a first mechanical strength and the second opening is formed in the first area, and the second area has a second mechanical strength that is larger than the first mechanical strength.

The disinfectant solution containing member 13 is provided partway on an opening path between the opening action start point 11s where the action of opening the packaging member 11 is started and the opening action end point 11e where the action of opening the packaging member 11 is ended.

As shown in FIG. 2, the disinfectant solution containing member 13 is provided sandwiched between the first sheet 11a and the second sheet 11b.

The pull portion 14 is pulled according to the action of opening the packaging member 11 that is sealed, and opens the disinfectant solution containing member 13. For example, the pull portion 14 is provided adjacent to the seal 12. The pull portion 14 of the present embodiment includes a first joining part 14a that joins the first sheet 11a and the disinfectant solution containing member 13, and a second joining part 14b that joins the second sheet 11b and the disinfectant solution containing member 13. Here, joining of the first joining part 14a and the second joining part 14b may be performed by adhesion, welding or the like. The pull portion 14 is thus formed integrally with at least a part of the disinfectant solution containing member 13.

The disinfectant solution containing member 13 and the pull portion 14 are provided at a position closer to an outer edge of the packaging member 11 than to a center of the packaging member 11. The first portion of the packaging member 11 may be between the outer edge of the packaging member 11 and the center of the packaging member 11. A part of the second opening may be closer to the center of the packaging member 11 as compared to the first opening. The disinfectant solution package 13 may be closer to the outer edge of the packaging member 11 than to the center of the packaging member 11. The endoscope 3 is placed inside the packaging member 11, next to the pull portion 14. The pull portion 14 is provided between the outer edge of the packaging member 11 and a region where the endoscope 3 is placed.

The action of opening the packaging member 11 is performed in a state where the opening action start point 11s is on an upper side in a gravitational direction G.

Note that, to describe a structure of the endoscope 3, FIG. 1 described above shows the endoscope 3 in such a manner that the operation section 32 is on top and the distal end portion 31a and the connector 33a are on bottom. However, as shown in FIG. 3 and FIGS. 5 to 7 described below, for example, the endoscope 3 inside the sterile medical device package 2 is actually arranged on an opposite side from the disinfectant solution containing member 13 inside the seal 12.

More specifically, the sterile medical device package 2 is provided with a mechanism for temporarily fixing the medical device such as the endoscope 3 at a specific position on the opposite side from the disinfectant solution containing member 13 inside the seal 12. Accordingly, at the time of holding the sterile medical device package 2 to open, it is natural to hold the sterile medical device package 2 with the opening action start point 11s on the upper side in the gravitational direction G and the medical device on a lower side in the gravitational direction G. In other words, the sterile medical device package 2 is designed such that the opening action start point 11s comes on the upper side and the medical device on the lower side at the time of opening.

When an upper end portion of the first sheet 11a and an upper end portion of the second sheet 11b are pinched and an external force f1 as shown in FIG. 2 is applied, the first sheet 11a and the second sheet 11b are pulled and separated on an outer edge side of the seal 12, for example. The force that separates the first sheet 11a and the second sheet 11b concentrates on the opening action start point 11s, and the seal 12 is opened from the opening action start point 11s side and opening of the packaging member 11 is started.

When an action of separating the first sheet 11a and the second sheet 11b to open the packaging member 11 reaches an opening start point 13s that is partway on the opening path, the first joining part 14a and the second joining part 14b are pulled, and the disinfectant solution containing member 13 is torn and opening is started, and the disinfectant solution 4 inside starts to leak out. The disinfectant solution 4 leaking out is poured over the endoscope 3 that is on the lower side in the gravitational direction G.

Accordingly, the disinfectant solution 4 and volatilized gas from the disinfectant solution 4 surround the endoscope 3, and even when the sterile medical device package 2 is opened, if the endoscope 3 is not yet taken out of the sterile medical device package 2, environmental bacteria such as floating bacteria, falling bacteria and the like in the air around the endoscope 3 are disinfected by effects of the disinfectant solution 4. Accordingly, living environmental bacterial may be prevented from getting attached to the endoscope 3 inside the sterile medical device package 2, and the endoscope 3 is kept in a sterile state.

Opening of the disinfectant solution containing member 13 is completed when the opening action reaches an opening complete point 13e that is partway on the opening path.

Note that a description is given above of an example where the packaging member 11 is opened from the opening action start point 11s side by pulling and separating the first sheet 11a and the second sheet 11b on the outer edge side of the seal 12, for example. However, the packaging member 11 may instead be opened in the following manner.

In other words, the packaging member 11 may be opened by pulling and separating the first sheet 11a and the second sheet 11b by pinching a center side of the packaging member 11 than the disinfectant solution containing member 13. In this case, the first joining part 14a and the second joining part 14b are pulled by application of an external force f2 as shown in FIG. 2, and the disinfectant solution containing member 13 is thus torn and opening is started.

At this time, by making the external force f2 to tear the disinfectant solution containing member 13 is smaller than the predetermined external force f1 to separate the seal 12, a state is achieved in which the disinfectant solution containing member 13 is torn but the seal 12 is not separated.

Accordingly, the disinfectant solution 4 may be poured over the endoscope 3 without being poured out of the packaging member 11. Moreover, the packaging member 11 may be shaken while the endoscope 3 is contained in the packaging member 11. This allows the disinfectant solution 4 to come into contact with a surface of the endoscope 3, and a sterilization effect may be increased.

Note that a structural part where it feels more difficult to open (a sensation similar to click sensing, the same applies below) than other parts of the seal 12 may be provided at a part corresponding to the opening start point 13s of the seal 12 by increasing joining strength, for example. A user may thus feel start of opening of the disinfectant solution containing member 13.

Furthermore, a structural part where it feels more difficult to open than other parts of the seal 12 may be provided at a part corresponding to the opening complete point 13e of the seal 12 by increasing joining strength, for example. The user may thus feel completion of opening of the disinfectant solution containing member 13.

Note that as a method of increasing joining strength to provide a structural part where it feels more difficult to open, any method among a method of increasing bonding strength, a method of increasing bonded area, a method of hardening bonding, and the like may be used.

When start of opening of the disinfectant solution containing member 13 and completion of opening are felt through sensation at the time of opening, pouring of the disinfectant solution 4 over the medical device may be reliably confirmed.

According to the first embodiment as described above, even when preparation for endoscopic examination, such as inspection of an endoscope processor, is performed after the sterile medical device package 2 is opened, the endoscope 3 is kept sterile while the endoscope 3 is contained inside the sterile medical device package 2, until the disinfectant solution 4 is completely volatilized and dissipated.

Accordingly, environmental bacteria that get attached to the insertion section 31 of the endoscope 3 at the time of insertion of the insertion section 31 into a living body may be greatly reduced. Note that, in the first embodiment, a volatile disinfectant solution is best used as the disinfectant solution 4, but a disinfectant solution with low volatility or with almost no volatility may also be used. A disinfectant solution with low volatility or with almost no volatility can wet the surface of the endoscope 3, and a sterilization effect may be achieved.

The medical device system 1 may thus reduce attachment of environmental bacteria to the medical device even when the sterile medical device package 2 is opened.

Second Embodiment

Figure 3:
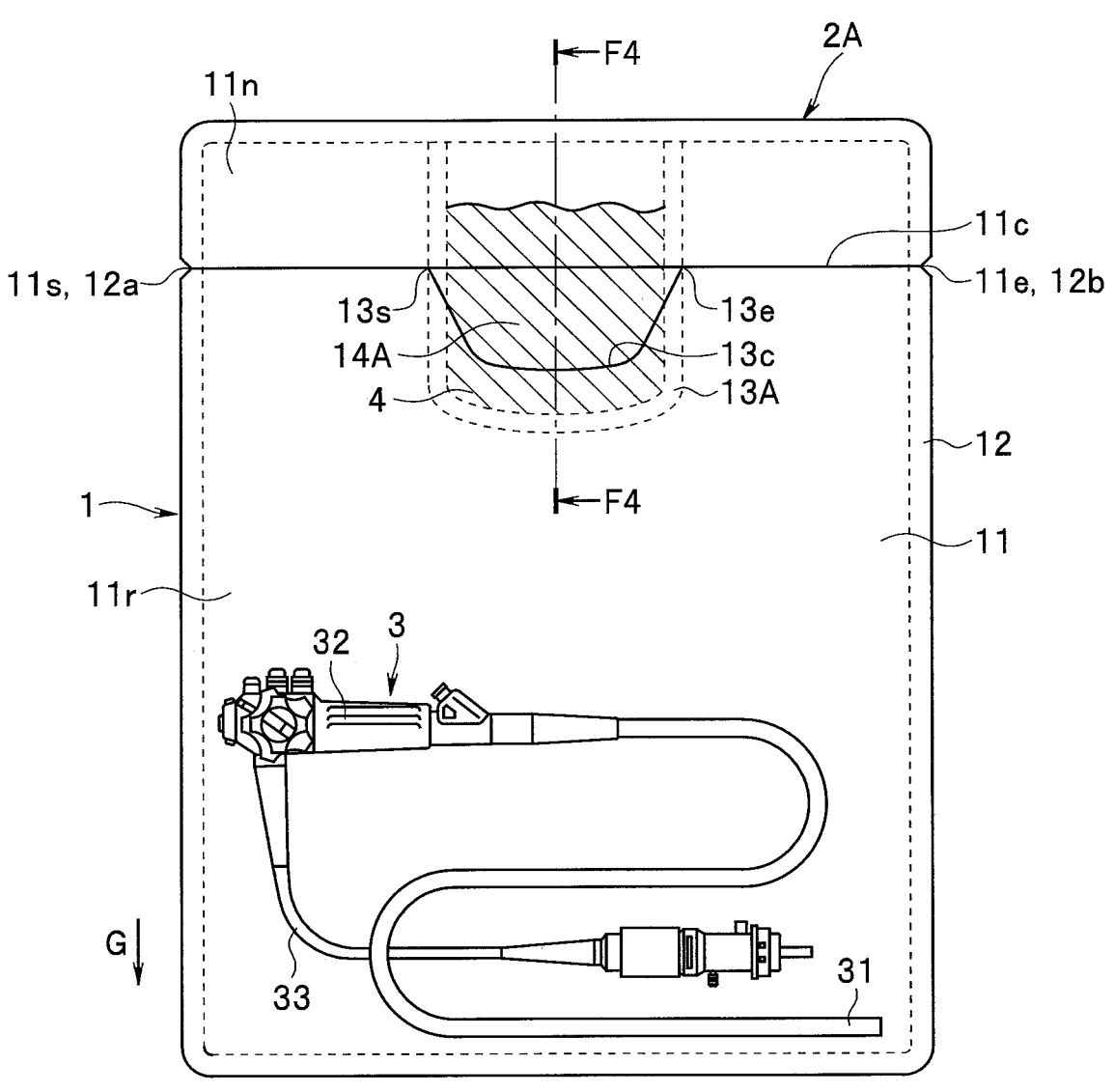
FIG. 3 is a diagram showing a medical device system according to a second embodiment of the present disclosure.
Figure 4:
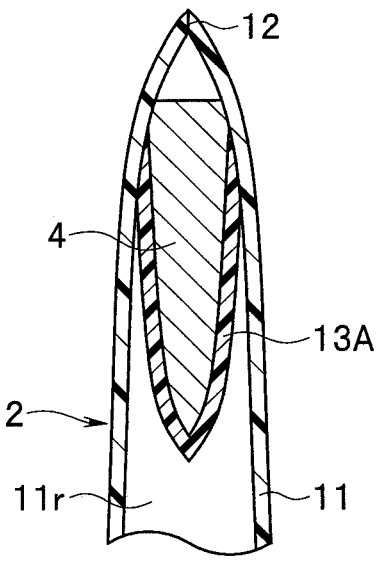
FIG. 4 is a cross-sectional view according to the second embodiment, taken along F4-F4 in FIG. 3.
Figure 5:
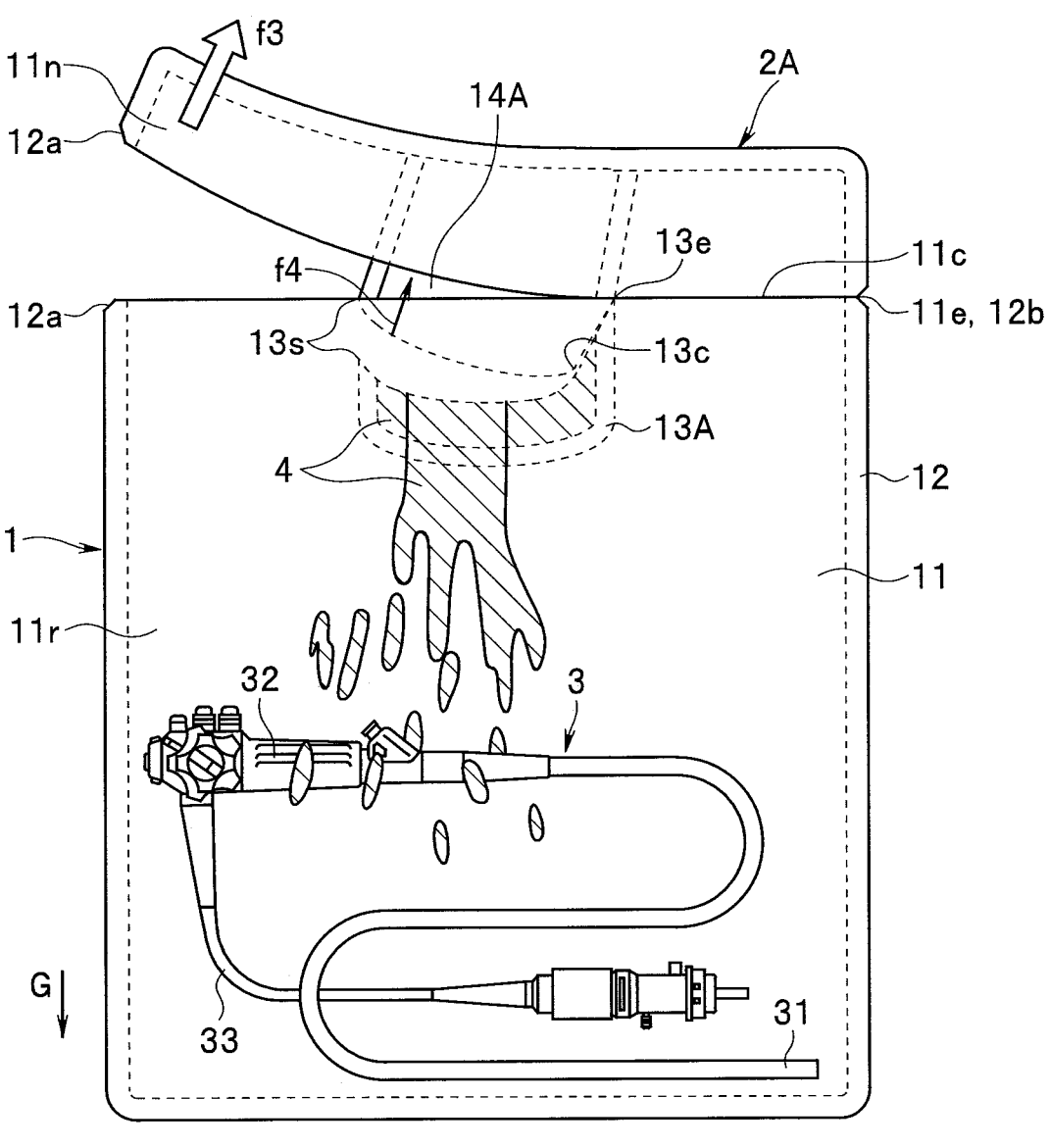
FIG. 5 is a diagram according to the second embodiment, showing a state where a pull portion is pulled according to an action of opening a packaging member and a disinfectant solution contained inside a disinfectant solution containing member is poured over an endoscope.

FIGS. 3 to 5 show a second embodiment of the present disclosure, and FIG. 3 is a diagram showing the medical device system 1 of the second embodiment. In the second embodiment, parts that are the same as the parts in the first embodiment will be denoted by same reference signs and description will be omitted as appropriate, and differences will be mainly described.

With the sterile medical device package 2 of the first embodiment, the seal 12 is provided somewhat to an inner circumferential side than the outer edge of the packaging member 11 such that an edge of the first sheet 11a and an edge of the second sheet b may be pinched. In contrast, with a sterile medical device package 2A of the medical device system 1 according to the present embodiment, the seal 12 that is formed as a heat seal, for example, is provided on the outer edge of the packaging member 11.

The medical device, such as the endoscope 3, is placed on one end side (on a lower end side in FIG. 3) in the space 11r inside the packaging member 11 sealed by the seal 12, and a disinfectant solution containing member 13A is provided on the other end side (on an upper end side in FIG. 3).

FIG. 4 is a cross-sectional view according to the second embodiment, taken along F4-F4 in FIG. 3. The disinfectant solution containing member 13A has a rectangular bag shape, for example, and the disinfectant solution 4 that is volatile is sealed inside the bag, as shown in FIG. 4. As shown in FIG. 3, the disinfectant solution containing member 13A is provided at a center part in a left-right direction of the packaging member 11, for example.

A notch 12a is provided on a left side surface on the outer edge of the packaging member 11, and a notch 12b is provided on a right-side surface. The notches 12a, 12b are each formed by cutting out a part of the outer edge of the seal 12 in a V-shape without reaching the space 11r inside the packaging member 11.

The packaging member 11 includes a linear unsealing line 11c that connects the notch 12a and the notch 12b. The unsealing line 11c is formed as a weak part with lower strength than other parts of the packaging member 11, and is provided at a position that crosses the disinfectant solution containing member 13A. For example, the unsealing line 11c is formed as a weak part by linearly reducing a thickness, by forming a cutting line that is not deep enough to penetrate the thickness, or by forming a crease. The notch 12a is formed in the outer edge of the packaging member 11. The notch 12a or 12b is a starting point for forming the first opening.

Positions where the unsealing line 11c reaches one end and the other end of the disinfectant solution containing member 13A are the opening start point 13s of the disinfectant solution containing member 13A and the opening complete point 13e of the disinfectant solution containing member 13, respectively.

FIG. 3 shows, as an example, a case where the notch 12a on the left side of the packaging member 11 is taken as the opening action start point 11s. In this case, positions where the unsealing line 11c reaches a left end and a right end of the disinfectant solution containing member 13A are the opening start point 13s and the opening complete point 13e, respectively. Moreover, the notch 12b on a right side of the packaging member 11 is the opening action end point 11e.

Note that, in the case where the notch 12b on the right side of the packaging member 11 is taken as the opening action start point 11s, positions where the unsealing line 11c reaches the right end and the left end of the disinfectant solution containing member 13A are the opening start point 13s and the opening complete point 13e, respectively, and the notch 12a on the left side of the packaging member 11 is the opening action end point 11e.

The disinfectant solution containing member 13A is provided with an opening line 13c, one end of which is connected to the opening start point 13s and the other end of which is connected to the opening action end point 11e. The opening line 13c is formed as a weak part with lower strength than other parts of the disinfectant solution containing member 13A. For example, the opening line 13c is formed as a weak part by linearly reducing a thickness, by forming a cutting line that is not deep enough to penetrate the thickness, or by forming a crease.

The opening line 13c is formed into a substantially U shape, for example, at a position closer to the center of the packaging member 11 compared to the unsealing line 11c connecting the opening action start point 11s and the opening action end point 11e.

Accordingly, when the medical device system 1 is disposed such that the endoscope 3 is on the lower side in the gravitational direction G, as shown in FIG. 3, the opening line 13c draws a curve that slopes downward from the opening start point 13s, then rises upward after reaching a lowest part, and ends at the opening action end point 11e.

A pull portion 14A is provided between the opening line 13c of the disinfectant solution containing member 13A and the unsealing line 11c. The pull portion 14A formed in the disinfectant solution containing member 13A includes the opening line 13c that is formed as a weak portion. In other words, the pull portion 14A is formed integrally with the disinfectant solution containing member. The pull portion 14A is provided at a position closer to the center of the packaging member 11 compared to the linear unsealing line 11c connecting the opening action start point 11s and the opening action end point 11e.

FIG. 5 is a diagram according to the second embodiment, showing a state where the pull portion 14A is pulled according to an action of opening the packaging member 11 and the disinfectant solution 4 contained inside the disinfectant solution containing member 13A is poured over the endoscope 3.

The packaging member 11 starts to be opened along the unsealing line 11c when an adjacent part 11n of the notch 12a or the notch 12b is pulled in a predetermined direction. The adjacent part 11n is a corner portion of edges of the packaging member 11, on an opposite side from the center of the packaging member 11 across the unsealing line 11c, for example. Furthermore, the predetermined direction is a direction of separating the adjacent part 11n from a side of the center of the packaging member 11 across the unsealing line 11c, for example.

As shown in FIG. 5, an external force f3 with which the unsealing line 11c that is a weak portion can be cut off is applied while pinching the adjacent part 11n of the notch 12a, for example. Then, the adjacent part 11n is pulled with the notch 12a as the opening action start point 11s, and the unsealing line 11c is gradually cut off from the notch 12a in a direction of the notch 12b. When cutting of the unsealing line 11c reaches the opening start point 13s, the pull portion 14A is pulled in a direction of being separated from the center of the packaging member 11.

A pulling force f4 is thus applied to the opening line 13c that is a weak portion of the pull portion 14A, and the opening line 13c starts to be cut off from the opening start point 13s.

When the medical device system 1 is arranged such that the endoscope 3 is on the lower side in the gravitational direction G, as shown in FIG. 5, the opening line 13c is positioned lower than the unsealing line 11c. Accordingly, even when the disinfectant solution 4 starts to leak from the opening line 13c that is cut off, the disinfectant solution 4 is poured over the endoscope 3 without leaking to outside of the packaging member 11.

Accordingly, as in the first embodiment, the disinfectant solution 4 and volatilized gas from the disinfectant solution 4 surround the endoscope 3, and the endoscope 3 is kept in a sterile state.

Then, the packaging member 11 continues to be cut off along the unsealing line 11c, and the disinfectant solution containing member 13A continues to be cut off along the opening line 13C. When the cut reaches the opening complete point 13e, opening of the disinfectant solution containing member 13A along the opening line 13c is complete.

Then, the unsealing line 11c continues to be cut off, and when the cut reaches the notch 12b that is the opening action end point 11e, opening of the packaging member 11 is ended.

Note that the sterile medical device package 2A shown in FIG. 3 is formed to be left-right symmetric, with the notches 12a, 12b provided on left and right sides, and the disinfectant solution containing member 13A positioned at a center portion in a left-right direction. Accordingly, same action and advantageous effect may be obtained by starting to open with either of the notches 12a, 12b as the opening action start point 11s.

Furthermore, strength of at least one of the opening start point 13s or the opening complete point 13e may be set higher than strength of the opening line 13c that is a weak portion. For example, when high strength is set for the opening start point 13s, the user may feel that opening of the disinfectant solution containing member 13A is started. Moreover, when high strength is set for the opening complete point 13e, the user may feel that opening of the disinfectant solution containing member 13A is completed. When start of opening of the disinfectant solution containing member 13A and completion of opening are felt through sensation at the time of opening in the above manner, pouring of the disinfectant solution 4 over the medical device may be reliably confirmed.

Note that an example is described above where the disinfectant solution containing member 13A is provided at a center of the packaging member 11 in the left-right direction, but the position in the left-right direction is not limited and may be to the left or the right in the left-right direction.

For example, the disinfectant solution containing member 13A may be provided close to the opening action end point 11e where the opening action ends. In this case, when the sterile medical device package 2A is designed such that a left side of the sterile medical device package 2A is the opening action start point 11s, the disinfectant solution containing member 13A may be provided on a right side where the opening action end point 11e is. Furthermore, when the sterile medical device package 2A is designed such that the right side of the sterile medical device package 2A is the opening action start point 11s, the disinfectant solution containing member 13A may be provided on the left side where the opening action end point 11e is. According to the second embodiment, the disinfectant solution 4 is poured over the endoscope 3 immediately after the sterile medical device package 2A is opened, and the endoscope 3 is thus sterilized. Moreover, there is an advantage that the disinfectant solution remaining in the packaging member 11 may be drizzled over a part where sterilization becomes particularly important, such as the insertion section 31.

Moreover, the disinfectant solution containing member 13A is not limited to be provided at a part of a left-right width of the sterile medical device package 2A, and may instead be provided across the entire left-right width. This allows the disinfectant solution to be uniformly poured over the entire endoscope 3. Note that, in this case, the disinfectant solution containing member 13A may be divided into a plurality of sections, and the disinfectant solution may be contained in each of the sections.

According to the second embodiment, approximately the same advantageous effects as the advantageous effects of the first embodiment described above may be obtained by providing the pull portion 14A that is pulled according to the opening action of the packaging member 11.

Third Embodiment

Figure 6:
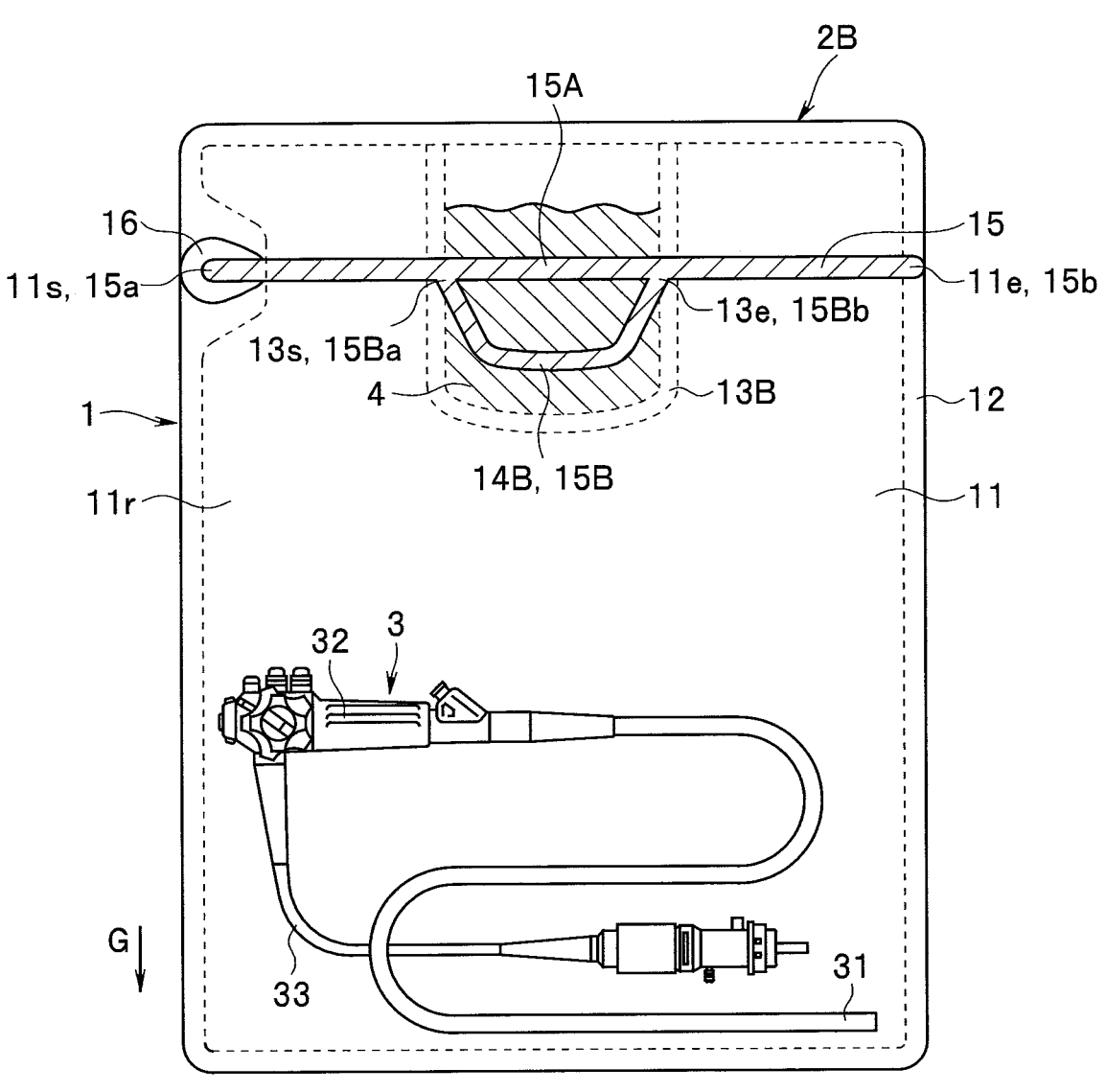
FIG. 6 is a diagram showing a medical device system according to a third embodiment of the present disclosure.
Figure 7:
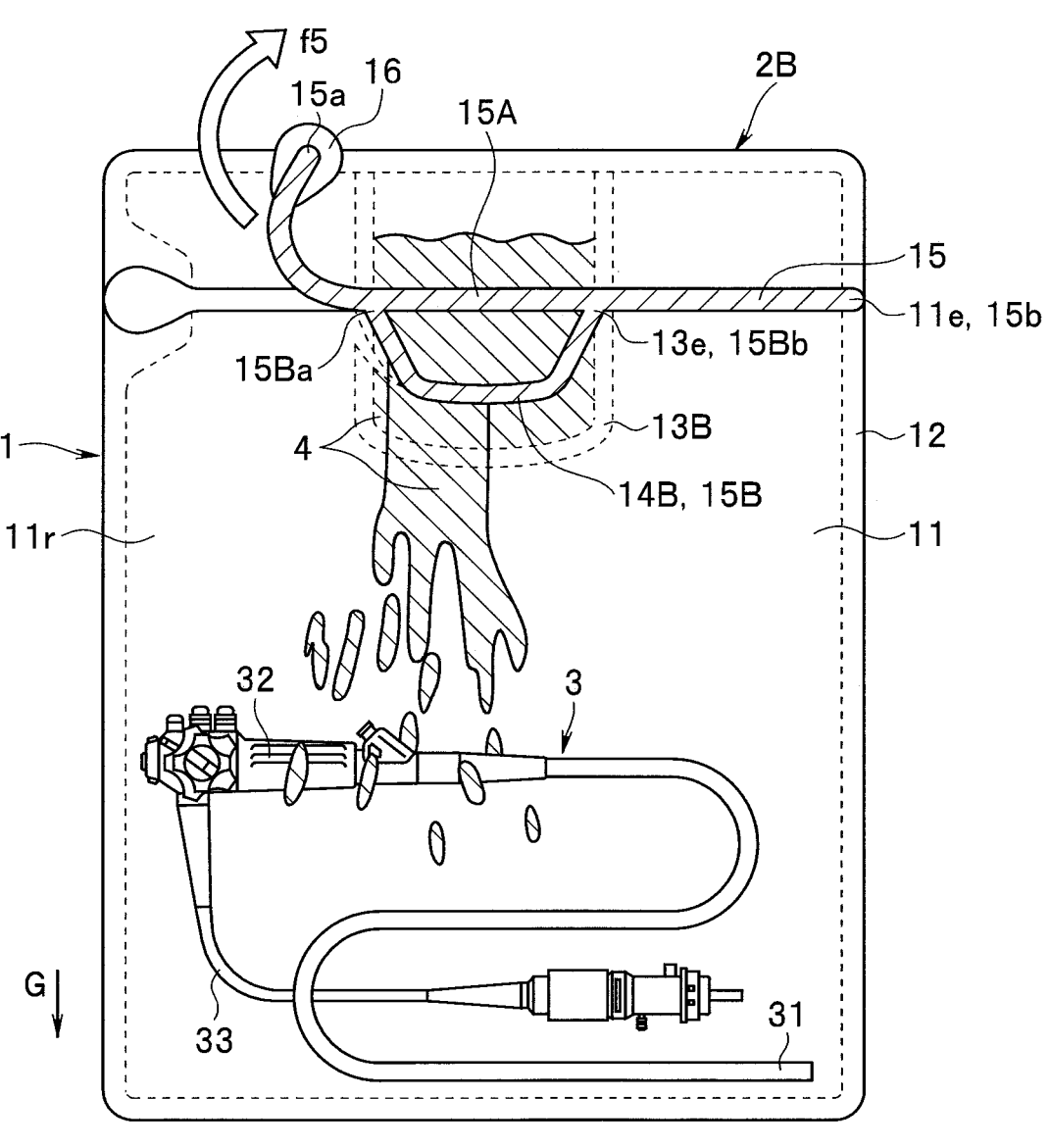
FIG. 7 is a diagram according to the third embodiment, showing a state where a pull portion is pulled according to an action of opening a packaging member and a disinfectant solution contained inside a disinfectant solution containing member is poured over an endoscope.

FIGS. 6 and 7 show a third embodiment of the present disclosure, and FIG. 6 is a diagram showing the medical device system 1 according to the third embodiment. In the third embodiment, parts that are the same as the parts in the first and second embodiments will be denoted by same reference signs and description will be omitted as appropriate, and differences will be mainly described.

A sterile medical device package 2B of the medical device system 1 includes the seal 12 that is formed as a heat seal, at an outer edge of the packaging member 11. The endoscope 3 as the medical device is placed on one end side in the space 11r inside the packaging member 11 that is sealed by the seal 12, and a disinfectant solution containing member 13B is provided on the other end side.

A tape 15 is joined to the packaging member 11, at a position that crosses the disinfectant solution containing member 13B. One end 15a of the tape 15 is the opening action start point 11s, and other end 15b is the opening action end point 11e. Note that a tag (tab) 16 is provided at the one end 15a of the tape 15 as the opening action start point 11s, for example. The tape 15 is used to open the packaging member 11 by being separated from the packaging member 11 to which the tape 15 is joined.

The tape 15 includes a tape main body 15A that is joined to the packaging member 11, and a branched tape 15B that is branched from the tape main body 15A. Note that the one end 15a and the other end 15b mentioned above are one end and the other end of the tape main body 15A. The branched tape 15B is joined to the disinfectant solution containing member 13B. The branched tape 15B is included in a pull portion 14B described later. In other words, the pull portion 14B of the third embodiment is joined to the disinfectant solution containing member 13B, and the pull portion 14B is formed integrally with the disinfectant solution containing member 13B.

The branched tape 15B includes a first end 15Ba and a second end 15Bb that are positioned at branching points from the tape main body 15A. The branched tape 15B branches from the tape main body 15A at the first end 15Ba and merges with the tape main body 15A at the second end 15Bb. The first portion of the packaging member 11 includes a first tape 15A, the second portion includes a second tape 15B connected to the first tape 15A. The second tape 15B may be connected to the first tape 15A at a starting point for forming the second opening. The second tape 15B may be formed as an integral part of the first tape 15A via a branch.

One of the first end 15Ba and the second end 15Bb corresponds to the opening start point 13s, and the other to the opening complete point 13e. In the example shown in FIG. 6, the first end 15Ba corresponds to the opening start point 13s, and the second end 15Bb to the opening complete point 13e.

The pull portion 14B of the present embodiment includes the branched tape 15B. The branched tape 15B is provided at a position closer to the center of the packaging member 11 than the tape main body 15A is. Accordingly, when the medical device system 1 is arranged such that the endoscope 3 is on the lower side in the gravitational direction G, the branched tape 15B is positioned lower than the tape main body 15A, as shown in FIG. 7.

FIG. 7 is a diagram according to the third embodiment, showing a state where the pull portion 14B is pulled according to an action of opening the packaging member 11 and the disinfectant solution 4 contained inside the disinfectant solution containing member 13B is poured over the endoscope 3.

When a tag 16 is grasped and an external force f5 is applied, and the tag 16 is pulled in a predetermined direction, the packaging member 11 starts to be opened due to detachment of the tape 15. The predetermined direction is a direction of separating the tag 16 from a surface of the packaging member 11, or a direction of bringing the tag 16 closer to the opening action end point 11e, for example.

When detachment of the tape 15 continues and reaches the opening start point 13s, detachment of the tape main body 15A from the packaging member 11 and detachment, from the disinfectant solution containing member 13B, of the branched tape 15B that is pulled by the tape main body 15A start to proceed at the same time.

When the branched tape 15B is detached from the disinfectant solution containing member 13B, the disinfectant solution containing member 13B opens, and the disinfectant solution 4 is poured onto the endoscope 3 that is on the lower side in the gravitational direction G.

At this time, because the branched tape 15B is positioned lower than the tape main body 15A in the gravitational direction G as described above, the disinfectant solution 4 is poured over the endoscope 3 without leaking to outside of the packaging member 11 even if the disinfectant solution 4 leaks from a part of the disinfectant solution containing member 13B where the branched tape 15B is detached.

Accordingly, as in the first and second embodiments, the disinfectant solution 4 and volatilized gas from the disinfectant solution 4 surround the endoscope 3, and the endoscope 3 is kept in a sterile state.

Then, as the detachment of the tape main body 15A from the packaging member 11 proceeds, detachment, from the disinfectant solution containing member 13B, of the tape 15B that is pulled by the tape main body 15A proceeds. When detachment of the tape 15 reaches the opening complete point 13e, opening of the disinfectant solution containing member 13B by the branched tape 15B is completed.

Then, the tape main body 15A continues to be detached from the packaging member 11, and opening of the packaging member 11 is ended when detachment reaches the other end 15b of the tape 15 that is the opening action end point 11e.

Note that, also in the present embodiment, as in each embodiment described above, by making at least one of the opening start point 13s or the opening complete point 13e more difficult to detach than other parts of the tape 15 and causing a sensation similar to click sensing to be generated, the user may feel at least start or completion of opening of the disinfectant solution containing member 13B.

Furthermore, FIGS. 6 and 7 show an example where the tape 15 is provided on one surface of the packaging member 11, in a manner of crossing the packaging member 11, but such an example is not restrictive. For example, the tape 15 may be provided extending from a front surface of the packaging member 11 in FIG. 6 to a rear surface. In this case, when detachment of the tape 15 on the front surface of the packaging member 11 reaches the right end in FIG. 6, the tape 15 is further detached on the rear surface of the packaging member 11, from the right end to the left end. According to such a configuration, the packaging member 11 is separated into two parts across the tape 15 by completely detaching the tape 15, thereby allowing the endoscope 3 to be easily taken out.

Moreover, also in the third embodiment, as in the second embodiment, arrangement of the disinfectant solution containing member 13B in the left-right direction is not strictly specified, and a size in the left-right direction is not strictly specified.

According to the third embodiment, approximately the same advantageous effects as the advantageous effects of the first and second embodiments described above may be obtained by using the tape 15.

According to the first to third embodiments, a sterilization method for a medical device as described below is also one of the embodiments.

A sterilization method for a medical device, the method including:

placing a medical device inside a packaging member that is bag-shaped;

placing, inside the packaging member, a disinfectant solution containing member containing a disinfectant solution;

sealing the packaging member;

causing the disinfectant solution containing member to be opened when the packaging member is opened; and sterilizing the medical device with the disinfectant solution.

According to the first to third embodiments, an opening method for a sterile medical device package as described below is also one of the embodiments.

An opening method for a sterile medical device package, the method including:

holding a packaging member inside which a disinfectant solution containing member containing a disinfectant solution and a medical device are sealed;

starting to open the packaging member by pulling the packaging member; and causing the disinfectant solution containing member to be opened according to an action of opening the packaging member.

According to the first to third embodiments, a sterilization method for a medical device as described below is also one of the embodiments. A method of opening the medical device system comprising:

holding the sterile medical device package; and opening the sterile medical device package by an opening operation. The portion of the disinfectant solution package 13 is fixed to the packaging member 11 such that the opening operation opens both the packaging member 11 and the disinfectant solution package 13. The disinfectant solution package 13 contains the disinfectant solution, and the method further comprises, after the opening operation, contacting a portion of the sterile medical device 3 with the disinfectant solution from the disinfectant solution package 13.

According to the first to third embodiments, a sterilization method for a medical device as described below is also one of the embodiments. A packaging method, comprising:

placing a sterile medical device 3 inside a package via a first opening;

placing a disinfectant solution inside the disinfectant solution package 13 placed in the package via a second opening; and sealing the first opening of the package and the second opening of the disinfectant solution package 13. A preferential opening portion simultaneously opens the package and the disinfectant solution package 13.

Note that the present disclosure is not limited to the above-described embodiments as they are, and in the practical phase, the present disclosure can be embodied by modifying the structural elements within a range not departing from the gist of the disclosure. Furthermore, various aspects of the disclosure can be achieved by appropriately combining the plurality of structural elements disclosed in the embodiments described above. For example, some structural elements may be removed from all the structural elements indicated in the embodiments. Furthermore, structural elements in different embodiments may be combined as appropriate. As described above, it should be understood that various modifications and applications are possible in a range not departing from the spirit of the disclosure.

Example 1. A sterile medical device package comprising:

a packaging member that is bag-shaped and inside which a sterile medical device is placed;

a seal that seals the packaging member;

a disinfectant solution containing member that is provided in a space inside the packaging member that is sealed by the seal, the disinfectant solution containing member containing inside a disinfectant solution; and a pull portion that is integrally formed with at least a part of the disinfectant solution containing member, wherein the pull portion opens the disinfectant solution containing member by being pulled according to an action of opening the packaging member.

Example 2. The sterile medical device package according to Example 1, wherein the disinfectant solution containing member is provided partway on an opening path between an opening action start point where the action of opening the packaging member is started and an opening action end point where the action of opening the packaging member is ended.

Example 3. The sterile medical device package according to Example 2, wherein opening of the disinfectant solution containing member is started when the action of opening the packaging member reaches an opening start point that is partway on the opening path, and is completed when the action reaches an opening complete point that is partway on the opening path.

Example 4. The sterile medical device package according to Example 1, wherein the packaging member is formed into a bag shape by sticking a first sheet and a second sheet together by the seal, and opening of the packaging member is started when the seal is opened by pulling and separating the first sheet and the second sheet.

Example 5. The sterile medical device package according to Example 4, wherein opening of the packaging member is started by pulling and separating the first sheet and the second sheet on an outer edge side of the seal of the packaging member.

Example 6. The sterile medical device package according to Example 4, wherein the disinfectant solution containing member is provided sandwiched between the first sheet and the second sheet, and the pull portion includes a first joining part that joins the first sheet and the disinfectant solution containing member, and a second joining part that joins the second sheet and the disinfectant solution containing member.

Example 7. The sterile medical device package according to Example 6, wherein the pull portion is provided adjacent to the seal.

Example 8. The sterile medical device package according to Example 3, wherein the opening action start point is a notch that is formed in an outer edge of the packaging member.

Example 9. The sterile medical device package according to Example 8, wherein opening of the packaging member is started by pulling an adjacent part of the notch in a predetermined direction.

Example 10. The sterile medical device package according to Example 9, wherein the pull portion is provided at a position closer to a center of the packaging member compared to a straight line connecting the opening action start point and the opening action end point.

Example 11. The sterile medical device package according to Example 10, wherein the pull portion includes a weak portion that is formed in the disinfectant solution containing member and that has lower strength than other parts of the disinfectant solution containing member.

Example 12. The sterile medical device package according to Example 11, wherein strength of at least one of the opening start point or the opening complete point is set higher than for the weak portion.

Example 13. The sterile medical device package according to Example 3, wherein the opening action start point is one end of a tape that is joined to the packaging member.

Example 14. The sterile medical device package according to Example 13, wherein the tape includes a tape main body that is joined to the packaging member, and a branched tape that is branched from the tape main body, the branched tape is joined to the disinfectant solution containing member, and the pull portion includes the branched tape.

Example 15. The sterile medical device package according to Example 14, wherein the branched tape includes a first end and a second end that are positioned at branching points from the tape main body, one of the first end and the second end corresponds to the opening start point and another one corresponds to the opening complete point, and the branched tape is provided at a position closer to a center of the packaging member compared to the tape main body.

Example 16. A medical device system comprising:

a medical device that is sterilized; and a sterile medical device package including a packaging member that is bag-shaped and inside which the medical device is placed, a seal that seals the packaging member to keep the medical device sterile, a disinfectant solution containing member that is provided in a space inside the packaging member that is sealed by the seal, the disinfectant solution containing member containing inside a disinfectant solution that is volatile, and a pull portion configured to open the disinfectant solution containing member by being pulled according to an action of opening the packaging member that is sealed.

Example 17. The medical device system according to Example 16, wherein the disinfectant solution containing member and the pull portion are provided at a position closer to an outer edge of the packaging member than to a center of the packaging member.

Example 18. The medical device system according to Example 17, wherein the medical device is placed inside the packaging member, adjacent to the pull portion, and the pull portion is provided between the outer edge and a region where the medical device is placed.

Example 19. The medical device system according to Example 16, wherein the medical device is an endoscope.

Example 20. The medical device system according to Example 19, wherein the endoscope is a single-use endoscope that is disposed of after being used once.

Example 21. A sterilization method for a medical device, the method comprising:

placing a medical device inside a packaging member that is bag-shaped;

placing, inside the packaging member, a disinfectant solution containing member containing a disinfectant solution;

sealing the packaging member;

causing the disinfectant solution containing member to be opened when the packaging member is opened; and sterilizing the medical device with the disinfectant solution.

Example 22. An opening method for a sterile medical device package, the method comprising:

holding a packaging member inside which a disinfectant solution containing member containing a disinfectant solution and a medical device are sealed;

starting to open the packaging member by pulling the packaging member; and causing the disinfectant solution containing member to be opened according to an action of opening the packaging member.

What is claimed is:

1. A sterile medical device package, comprising:

a packaging member including a first sheet and a second sheet connected together by a seal into a bag shape having an interior space;

a disinfectant solution package located in a first section of the interior space and is between the first sheet and the second sheet; and

a pull portion located adjacent to the seal and joining the package member and the disinfectant solution package, wherein the pull portion is configured to simultaneously open the packaging member and the disinfectant solution package under an applied external force, wherein a second section of the interior space is configured to contain a sterile medical device, and wherein the disinfectant solution package contains a disinfectant solution.

2. The sterile medical device package according to claim 1, wherein when the packaging member is open, the packaging member includes a first opening, and wherein when the disinfectant solution package is open, the disinfectant solution package includes a second opening.

3. The sterile medical device package according to claim 2, wherein the first opening includes at least a portion of the second opening.

4. The sterile medical device package according to claim 3, wherein the second opening includes a first end and a second end, and wherein the first end is a starting point of the second opening and the second end is an ending point of the second opening.

5. The sterile medical device package according to claim 4, wherein a mechanical strength of the disinfectant solution package at the starting point is a first mechanical strength, wherein a mechanical strength of the disinfectant solution package at the ending point is a second mechanical strength, and wherein the first mechanical strength is less than the second mechanical strength.

6. The medical device system according to claim 4, wherein the first end is between an outer edge of the packaging member and a center of the packaging member.

7. The sterile medical device package according to claim 2, wherein the pull portion includes a first joining part that joins the first sheet of the packaging member and the disinfectant solution package, and a second joining part that joins the second sheet of the packaging member and the disinfectant solution package, wherein the first joining part includes a first tape, and wherein the second joining part includes a second tape.

8. The sterile medical device package according to claim 7, wherein the second tape is connected to the first tape at a starting point of the second opening.

9. The sterile medical device package according to claim 2, wherein the includes a third sheet and a fourth sheet, wherein a first part of the third sheet is fixed to the first sheet, wherein a first part of the fourth sheet is fixed to the second sheet,

wherein a second part of the third sheet is fixed to a second part of the fourth sheet, and wherein the second opening is formed by separating one of (i) a portion of the first part of the third sheet from the first sheet, (ii) a portion of the first part of the fourth sheet from the second sheet in conjunction with separating the first sheet and the second sheet, and (iii) a portion of the second part of the third sheet from a portion of the second part of the fourth sheet.

10. The sterile medical device package according to claim 2, wherein the packaging member includes a notch that is formed in an outer edge of the packaging member, and wherein the notch is a starting point the first opening.

11. The sterile medical device package according to claim 2, wherein a part of the second opening is closer to a center of the packaging member as compared to the first opening.

12. The sterile medical device package according to claim 2, wherein the includes a first area and a second area, wherein the first area has a first mechanical strength and the second opening is formed in the first area, and wherein the second area has a second mechanical strength that is larger than the first mechanical strength.

13. The sterile medical device package according to claim 1, wherein the disinfectant solution package is closer to an outer edge of the packaging member than to a center of the packaging member.

14. A medical device system, comprising:

a medical device that is sterilized; and the sterile medical device package according to claim 1, wherein the medical device is contained within the sterile medical device package.

15. The medical device system according to claim 14, wherein the medical device is an endoscope.

16. The medical device system according to claim 15, wherein the endoscope is a single-use endoscope.

17. The sterile medical device package according to claim 1, wherein the pull portion includes a first joining part that joins the first sheet of the packaging member and the disinfectant solution package, and a second joining part that joins the second sheet of the packaging member and the disinfectant solution package, wherein the first joining part joins the first sheet of the packaging member and the disinfectant solution package by adhesion or welding, and wherein the second joining part joins the second sheet of the packaging member and the disinfectant solution package by adhesion or welding.

18. The sterile medical device package according to claim 1, wherein the pull portion is formed integrally with at least a part of the disinfectant solution package, and wherein the pull portion is located closer to an outer edge of the packaging material than to a center of the packaging material.

* * * * *